(12) United States Patent
Petrus

(10) Patent No.: US 8,017,657 B1
(45) Date of Patent: Sep. 13, 2011

(54) COMPOSITION FOR THE TREATMENT AND PREVENTION OF ENDOTHELIAL DYSFUNCTION

(75) Inventor: Edward Joseph Petrus, Austin, TX (US)

(73) Assignee: Advanced Medical Instruments, Austin, TX (US)

( * ) Notice: Subject to any disclaimer, the term of this patent is extended or adjusted under 35 U.S.C. 154(b) by 913 days.

(21) Appl. No.: 11/978,505

(22) Filed: Oct. 30, 2007

Related U.S. Application Data

(63) Continuation-in-part of application No. 09/947,674, filed on Sep. 7, 2001, now Pat. No. 6,596,708, and a continuation of application No. 10/436,528, filed on May 14, 2003, now Pat. No. 6,930,099, and a continuation of application No. 11/057,671, filed on Feb. 15, 2005, now Pat. No. 7,846,914.

(51) Int. Cl.
*A61K 31/137* (2006.01)
*A61K 31/24* (2006.01)
*A61K 31/192* (2006.01)
*A61K 31/7008* (2006.01)

(52) U.S. Cl. ........................ 514/653; 424/465

(58) Field of Classification Search .................. None
See application file for complete search history.

(56) References Cited

U.S. PATENT DOCUMENTS

| | | | | | |
|---|---|---|---|---|---|
| 5,948,443 | A | * | 9/1999 | Riley et al. | 424/643 |
| 6,149,938 | A | * | 11/2000 | Bonadeo et al. | 424/464 |
| 6,333,304 | B1 | * | 12/2001 | Bath et al. | 514/2 |
| 6,589,943 | B2 | * | 7/2003 | Byun et al. | 514/56 |
| 6,841,544 | B2 | * | 1/2005 | Gelber et al. | 514/54 |

OTHER PUBLICATIONS

Gurfinkel, E. et al "Low molecular weight heparin versus regular heparin . . . " J. Am. Coll. Cardiol. (1995) vol. 26, No. 2, pp. 313-318.*
Cheng, J. et al "Nonsteroidal anti-inflammatory drugs and aspirin . . . " Am. J. Ther. (1997) vol. 4, pp. 62-65.*
Rawas-Qalaji, M. et al "Epinephrine for the treatment of anaphylaxis . . . " Biopharm. Drug Disp. (2006) vol. 27, 427-435.*
Appel, D. et al "Epinephrine improves expiratory flow rates in patients with asthma . . . " J. Allergy Clin. Immunol. (1989) vol. 84, pp. 90-98.*
Wolfe, M. et al "Gastrointestinal toxicity of nonsteroidal antiinflammatory drugs" New Engl. J. Med. (1999) vol. 340, No. 24, pp. 1888-1899.*
Schmitz T, et al, Oral heparin dleivery and in vivo evaluation of a stomach-targeted mucoadhesive delivery system. J. Pharm Sci., May 2005;94(5):966-73.
Petrus, EJ, Aspirin—The Golden Pill, 2009, pp. 103-109.

* cited by examiner

*Primary Examiner* — Leigh Maier

(57) ABSTRACT

A composition and method for pain relief and the treatment and prevention of endothelial dysfunction the cause of atherosclerosis, cardiovascular disease, hypertension, and stroke in mammals comprising a therapeutically effective amount of anti-inflammatory agents comprising; NSAIDs, an amino sugar and a zinc compound combined with dietary supplements that may enhance longevity.

1 Claim, No Drawings

COMPOSITION FOR THE TREATMENT AND PREVENTION OF ENDOTHELIAL DYSFUNCTION

This application is a continuation-in-part of Ser. No. 09/947,674 filed Sep. 7, 2001, now U.S. Pat. No. 6,596,708, and a continuation of Ser No. 10/436,528 filed on May 14, 2003, now U.S. Pat. No. 6,930,099, and a continuation of Ser. No. 11/057,671 now U.S. Pat. No. 7,846,914 filed on Feb. 15, 2005.

FIELD OF INVENTION

This invention involves compositions of therapeutic agents for pain relief and the treatment and prevention of disorders associated with endothelial dysfunction.

BACKGROUND OF THE INVENTION

Endothelial cells are mesodermally derived, simple squamous epithelial cells that line the heart, blood and lymph vessels, line any closed cavity (peritoneal, pleural, pericardial, synovial) and line the intestinal tract. Endothelial cells of blood vessels have both mechanical and functional properties. They provide a barrier effect to the penetration of blood components into the vessel wall and have endocrine functions.

Vascular endothelium is a multi-functional barrier separating blood from interstitium. It plays a role in coagulation, inflammation, angiogenesis and has vasomotor functions. Endothelial dysfunction can be considered as an initial stage of atherosclerosis. Malik J, Melenovsky V, Wichterle D, Function and dysfunction of the endothelium, *Cas Lek Cesk* 2000 Apr. 12; 139(7):197-202. Endothelium dysfunction is recognized as an early event in the pathogenesis of cardiovascular disease, and linked to hypertension, diabetes mellitus and oxidative stress. Pepine C J, Clinical implications of endothelial dysfunction, *Clin Cardiol* 1998 November; 21(11):795-9.

Endothelial dysfunction is characterized by a loss of barrier function and an infiltration of cellular material into the vascular wall and loss of physiological vascular tone. There is a loss of nitric oxide mediated physiological vasodilation, increased endothelial adhesion and migration of leucocytes and macrophages into the subendothelial vascular wall. Hypoxia, shear forces and oxidative stress trigger events for endothelial dysfunction. Disorders associated with endothelial dysfunction may occur in any endothelial cells and include; hypertension, atherosclerosis, diabetes, immune system dysfunction, infections, inflammations, macular degeneration, cardiovascular disease and stroke.

SUMMARY OF THE INVENTION

This invention relates to a method and compositions for pain relief and the treatment and prevention of disorders associated with endothelial dysfunction consisting of anti-inflammatory agents and dietary supplements.

DETAILED DESCRIPTION OF THE INVENTION

Each year 1.5 million Americans suffer heart attacks (myocardial infarction) and 500,000 die of that first attack, with 48% being females. Most of the 500,000 deaths occur within 2 hours after chest pain or other symptoms. In Britain half of all heart attack patients die within two hours of symptom onset and two-thirds of the deaths occur before admission to the hospital. Rawles J, *Pre-Hospital Immediate Care* 1997; 1:12-18. During this critical 120 minute period, coronary thrombosis could be eliminated and the heart attack prevented if the thrombus could be averted. While the nation's death rate from heart attacks peaked in the 1960s, when the death rate from heart disease was 307.4 per 100,000 people, the rate has plummeted to 134.6 in 1996, but myocardial infarction still ranks as the nation's leading killer. Coronary artery disease (CAD) affects 13.5 million Americans, a million have survived heart attacks, 7 million have angina (myocardial ischemia), 600,000 have undergone coronary bypass surgery and 2,000 have had heart transplants. The economic burden is estimated at $150 billion annually. Tindall W N, *Business & Health* February 1998.

The vascular endothelium modulates blood vessel tone by secreting a variety of dilating and constricting substances. Dilating agents include nitric oxide (NO), prostacyclin, bradykinin, and endothelium-derived relaxing factor (EDRF) and heparinoids; constricting agents include endothelin, superoxide anion, endothelium-derived constricting factor, locally produced antiotensin II, and thromboxane. These agents not only control and alter vascular tone, but also can affect platelet adhesion and aggregation, influence thrombogenicity of the blood, and participate in cell proliferation and the development and progression of atherosclerosis.

Injury to endothelial cell function, primarily resulting from increased oxidant stress within the endothelium, leads to a cascade of events beginning with activation of vascular cytokines such as interleukin-1 (IL-1) and tumor necrosis factor-α (TNF-α) and proceeding to expression of adhesion molecules on the cell surface that include vascular cell adhesion molecule-1 (VCAM-1), intercellular adhesion molecule-1 (ICAM-1), and endothelial-leucocyte adhesion molecule (ELAM), which attracts monocytes and other leucocytes to adhere to the endothelial surface. Adherence is followed by infiltration of mononuclear cells into the vascular wall, together with activation of monocyte chemoattractant protein-1 (MCP-1), leads to scavenging of oxidized low-density lipoproteins (LDL), formation of lipid-laden foam cells, and development or progression of atherosclerotic plaque. Activation of prothrombogenic stimuli and inactivation of fibrinolytic factors with endothelial dysfunction predisposes these blood vessels to thrombosis. Quyyumi A A, *Am J of Med* 1998; 105(1A):32S-39S.

Vascular injury triggers thrombosis and a proliferative response. By the release of tissue factor and exposure of subendothelial matrix, the coagulation and platelet pathways are activated and a thrombus is formed, either on a micro or macroendoluminal level. Additionally, platelet activation leads to a variety of mitogens, growth-promoting factors, and cytokines. Potent mitogens, such as platelet-derived growth factor and fibroblast growth factor, cause smooth muscle cells, fibroblasts, inflammatory cells, and endothelial cells to participate in reendothelialization. Smooth muscle cell and fibroblast proliferation and migration result from signal transduction pathways initiated by factors biding to their specific cell-surface receptor. Smooth muscle cells and fibroblasts migrate from the media to the intimal surface. Smooth muscle cells are phenotypically transformed to the synthetic subtype and secrete an extracellular matrix consisting of proteoglycans. Ward S R, Topol E J, *Resident & Staff Physician* 1995; 41(3):11-18.

British scientists have reported a well-established link between inflammation and cardiovascular events mediated by inflammation-induced dysfunction of the arterial endothelium. Even mild systemic inflammatory responses are associated with significant alteration in endothelial function which lead to increased cardiovascular risk. Hingorani A D, et al., *Circulation* 2000; 102:994-999.

Thrombus formation is the proximate cause of myocardial infarction, but atherosclerosis, the chief underlying cause, is a chronic disease that progresses over decades of life. Inflammation has a role in both the initiation and the progression of atherosclerosis, and anti-inflammatory agents have a role in the prevention of cardiovascular disease.

Atherosclerosis may be considered as an aberrant form of would-healing in arteries. Repeated minor trauma, leading to subendothelial hemorrhage, may well account for the tendency of atherosclerosis to occur mostly at major blood vessel flexion sites and at sites of mechanical stress, such as the carotid sinus or the bifurcation of the carotid artery. The positive injury potential resulting from petechial hemorrhages in the vascular intima will attract negatively charged platelets an leucocytes and will lead to a layered thrombus formation. Gaps between the endothelial cells of the intima will allow the insinuation of monocytes beneath the endothelium, where it seems they can become transformed into macrophages and engulf oxidized LDL to become foam cells and lead to the formation of the atherosclerotic plaque.

C-reactive protein (CRP) is a natural substance that results from an inflammatory response to injury of infection by mobilizing white blood cells. CRP is an acute-phase reactant that is a biomarker for underlying systemic inflammation, reported in patients with acute ischemia or myocardial ischemia and found to predict recurrent ischemia in those with unstable angina. Base-line levels of CRP in apparently healthy men can predict the risk of the first myocardial infarction and ischemic stroke. Previous infection with *Chlamydia pneumonia, Heliobacter pylori*, herpes simplex virus, or cytomegalovirus may be the source of the chronic inflammation detected by CRP. An elevated CRP level is related to inflammation, and increased inflammation is noted for many diseases, such as cancer, cardiovascular disease, infection, connective tissue diseases and injuries. Elevated CRP reflects an increased production of proinflammatory cytokines such as interleukin-6, which may be contributing to the pathophysiology of disease either directly or indirectly through their relationship to other important components of inflammation, thrombosis, or fibrinolysis. Kuller L H, Tracy R P, *Arteriosclerosis, Thrombosis, and Vascular Biology* 2000; 20(4):901

The Physicians Health Study (PHS) indicates that healthy men with baseline levels of CRP in the highest quartile had a threefold increase in risk of developing future myocardial infarction and twice the risk of developing stroke. These risk estimates were stable over an 8-10 year follow-up period, were not modified by smoking status, and were independent of other cardiovascular risk factors, including total and HDL cholesterol, triglycerides, lipoproteins and fibrinogen. Elevated baseline levels of CRP are also associated with a fourfold increase in the risk of developing clinically severe peripheral arterial disease, again independent of usual risk factors. Plasma levels of ICAM-1 are elevated many years in advance of a first-ever myocardial infarction and that levels of ICAM-1 correlate with CRP. Cellular adhesion molecules, such as ICAM-1, are critical in the adhesion of circulating leucocytes to the endothelial cell and subsequent endothelial transmigration, and provide evidence that cellular mediators of inflammation have a critical role in atherogenesis. CRP levels increase with increasing prevalence of exposure to *Heliobactor pylori*, the bacteria responsible for gastric ulcers. Ridker P M, *Circulation* 1998; 97:1671-1674.

Chronic subclinical infection with *Chlamydia pneumoniae, Heliobacter pylori*, chronic bronchitis, and chronic dental sepsis have been associated with raised values of CRP and have been implicated as risk factors for coronary heart disease. Mendall M A, *BMJ* 1998; 316:953-954. During acute unstable angina, which if believed to be an immune system-mediated inflammatory disorder, patients had significantly greater levels of CRP and helper T-cells and significantly reduced levels of suppressor T-cells. Caligiuri G, *J Am Coll Cardiol* 1998; 32:1295-1304.

*H pylori* is a spiral gram-negative rod that resides beneath the gastric mucus layer adjacent to epithelial cells. It causes a chronic mucosal inflammation and associated with peptic ulcer disease. *H pylori* is treated with antibiotics and bismuth or bismuth containing compounds such as bismuth subsalicylate. Tierney Jr. L M, McPhee S J, Papadakis M A, Current Medical Diagnosis and Treatment, Appelton & Lange, $3^{rd}$ ed 1994 p. 490.

Over 50% of those over age 60 and about 20% of those under age 40 are infected with *H. pylori. H. pylori* eradication may reverse the severity of aspirin-induced gastric injury. Extracts from cranberry, grape seed and blueberry have been shown to inhibit the adhesion of *H. pylori* to the gastric mucosa and can inhibit *H. pylori* in vitro. Vattem, D A et al *Process Biochemistry* 2004. Cranberry juice raises HDL cholesterol levels, inhibits the binding of *H. influenza* pili to buccal cells and controls gingival and periodontal diseases. Weiss E I, et al *J Am Dent Assoc* 1998 December; 129(12): 1719-23.

*H. pylori* colonize in the stomach weakening the lining and making the stomach vulnerable to irritation from natural stomach acids. *H. pylori* causes about nine out of ten duodenal ulcers and more than eight out of ten gastric ulcers.

Probiotics have the potential to minimize gastrointestinal conditions such as diarrhea, irritable bowel syndrome (IBS) and inflammatory bowel disease. Children who were treated for *H. pylori* with an antibiotic cocktail with probiotic (*Lactobacillus reuteri*) had less intestinal distress. IBS has been associated with decreased nonpathogenic colonies and increased Clostridium species. *Bifidobacterium infantis* have shown promise in treating IBS when used with gut-directed antibiotics.

Probiotics not only inhibit *H. Pylori* but also help prevent ulcers caused by the use of NSAIDs. Probiotics that may be combined with or used with aspirin include but are not limited to *Bifidobacterium lactis, Lactobacillus rhamnosus, Lactobacillus acidophilus, Lactobacillus reuteri, Lactobacillus paracasei, Bifidobacterium, Streptococcus thermophilus, Saccharomyces boulardii*, and others. Prebiotics are nondigestible substances that, when consumed, provide a beneficial physiological effect on the host by selectively stimulating the favorable growth or activity of a limited number of indigenous bacteria. Prebiotics may also be incorporated into a fast dissolving tablet to prevent *H. pylori* infections.

CRP concentrations were increased in about 75% of patients within 24 hours after ischemic stroke, and higher values were significantly associated with large infarct size. Di Napoli M, *BMJ* 2001; 322:1605. In 1950, the stroke death rate per 100,000 was 88.8. In 1996, it was 26.5. Stroke is the third leading cause of death (after heart disease and cancer). Americans suffer about 500,000 strokes each year and 150,000 stroke deaths. Cerebral thrombosis and cerebral embolism, known as ischemic stroke, account for about 80% of strokes. Cerebral thrombosis often occurs at night or first thing in the morning when blood pressure is normally low. About one-third of those who experience a transient ischemic attack (TIA) have a stroke within five years. Half of the post-TIA strokes occur within a year, 20% within one month. TIAs double the risk of heart attack. Those on ASA had 42% fewer strokes. It has been reported that immediate use of ASA be considered in all patients with acute ischemic stroke. Sandercock P A G, *Lancet* 1997; 349:1563-1565, 1569-1581.

Many of the current studies point to an inflammatory etiology for cardiovascular and cerebrovascular disorders. Anti-inflammatory agents have shown benefits for the treatment and prevention of these endothelial dysfunction diseases. This invention provides a composition to overcome the obstacles inherent in the prior approaches.

Acetylsalicylic acid (ASA) has been known to treat and prevent cardiovascular disease by reducing thrombosis, but the real effect is as an anti-inflammatory agent. ASA inhibits cyclo-oxygenase in both platelets and endothelial cells. At low doses ASA inhibits the formation of thromboxane A2 (TXA2), a potent vasoconstrictor and platelet agonist formed via cyclo-oxygenase-dependent pathway in platelets. At higher doses, ASA has been shown to block the formation of prostacyclin (PGI2), a vasodilator and inhibitor of platelet aggregation, in endothelial cells.

The use of ASA for the primary prevention of CAD was examined in the PHS in which 22,000 US male physicians were observed for about 5 years. Those who took 325 mg of ASA every other day had a 44% reduction in the incidence of first myocardial infarction, and a 25% reduction in the incidence of subsequent myocardial infarction, stroke, and death from cardiovascular causes. Milani R V, Lavie C J, *Postgraduate Medicine* 1996; 99(2):109-120. The rates of myocardial infarction were lower for those on acetylsalicylic acid (ASA) for all levels of CRP. Ridker P M, et al, *NEJM* 336 (14):973-979.

NSAIDs fall into seven major classes: proprionic acid derivatives, indole derivatives, fenamates, pyrrolealkanoic acids, pyrazolone derivatives, oxicams and salicylic acids. NSAIDs for purposes of this invention are selected from, but not limited to acetylsalicylic acid, ibuprofen, naproxen and ketoprofen. Most develop some erosions in the stomach after each dose. The number of NSAID users presenting with serious GI complications is low (1-2%), but the high usage of NSAIDs means the number affected is large. The annual death rate amongst patients with rheumatoid and osteoarthritis due to serious adverse consequences of GI ulceration (perforation and hemorrhage) has been estimated at 16,500 in the US alone.

High gastric acidity contributes to NSAID injury to the stomach and duodenal bulb. Most NSAIDs are weak acids (pKa values 3.5 to 6) existing in a non-ionized form at low pH, and are lipid soluble. They readily diffuse into surface cells and become trapped at the higher intracellular pH. This accumulation causes local toxicity. Gastric acid and possibly pepsin, appears to deepen some of the superficial lesions that occur with NSAIDs. Most superficial lesions repair within 1-2 hours, but some patches of damaged tissues do not repair in time to prevent deeper tissue destruction The GI tract protects itself from damaging mechanical and other stresses by producing and secreting onto epithelial surfaces a layer of lubricating mucus. Most GI pathology is probably related to the decreased production of mucus or breaking in the mucus layer. Mucus secretion and successful resealing occur simultaneously, and both require that external calcium be present during a plasma membrane disruption.

The incidence of acute peptic ulcer bleeding can be reduced by the addition of agents that suppress gastric acid formation, that include by not limited to proton pump inhibitors, acid pump inhibitors, H2-receptor antagonists, misoprostol and magnesium. Proton pump inhibitors have been shown to be effective to possible NSAID gastric injury. Leontiadis G I, et al *The Cochrane Library* Issue 4, 2004, John Wiley & Sons. The use of a proton pump inhibitor (heartburn pill) was also shown to prevent recurrent ulcer bleeding when ASA was combined with esomeprazole (Nexium) as opposed to using clopidogrel (Plavix). Chan F K L, et al *NEJM;* 2005; 352(3):238-244. Many investigators believe that the active agent in esomeprazole and omeprazole (Prilosec) is magnesium, which also has buffering properties.

The critical factor is how fast ASA is absorbed to reduce thrombosis within the 20 minute time frame. Myocardium (heart muscle) begins to undergo irreversible injury within 20 minutes of ishchemia and a wavefront of death sweeps from the inner to the outer layers of myocardium during a 3 to 6 hour period. The repair process requires two months to complete. Enteric-coated ASA takes about 60 minutes to reach peak blood levels; regular ASA reaches peak blood levels in 30 minutes; but chewing an ASA tablet reaches blood levels and inhibits platelet activity in 5 minutes. Undissolved tablets and large particles that adhere to the gastric mucosa result in lesions. Micropulverized ASA particles, 100-600 μm, cause fewer lesions because they diffuse readily reducing contact with the gastric mucosa. In a fast dissolving tablet, ASA is absorbed by the buccal mucosa and only small particles are swallowed into the esophagus.

Aspirin reduces cardiac vegetations that evolve in experimental *Staph aureus* endocarditis. It is postulated that aspirin's antiplatelet aggregation is combining with its antibacterial effect. Kupferwisser L I, et al *Circulation* 1999 June 199; 21:2791-7. The dosage of ASA for the present invention consists of 80-120 mg in a fast dissolving tablet which may be repeated when mixed with the amino sugar and zinc compound.

A number of patents disclose the use of ASA, primarily as analgesics both systemically and topically. Cotty et al, U.S. Pat. No. 4,049,803, discloses a composition of acetaminophen, ASA and caffeine. Patel, U.S. Pat. No. 4,867,984, discloses beads of ASA or acetaminophen coated with PVP. Frisbee, U.S. Pat. No. 4,970,081, discloses a formulation for a controlled release aspirin tablet. Bru et al, U.S. Pat. No. 5,437,874, discloses a composition of ASA or carbasalate calcium, metoclopramide, a hydrophilic polymer, anhydrous magnesium citrate and lactose. Eickhoff et al, U.S. Pat. No. 5,518,738, discloses NSAID particles coated with PVP. Liversidge et al, U.S. Pat. No. 5,552,160, discloses surface modified NSAID nanoparticles. Moshyedi, U.S. Pat. No. 5,770, 215, discloses a vitamin supplement with ASA. Medford et al, U.S. Pat. No. 5,846,959, discloses a method for treating CVD with PUFA and CV drugs. Riley et al, U.S. Pat. No. 5,948, 443, discloses a method for treating nutritional losses and heart disease with ASA, multivitamins and minerals. Noack et al, U.S. Pat. No. 5,973,011, discloses a method of treating endothelial dysfunction with PETN and active compounds to treat CVD. Weissman et al, U.S. Pat. No. 6,121,249, discloses a method for treating CVD with ASA, antioxidants and vitamins. Calanchi et al, U.S. Pat. No. 6,261,602 B1, discloses a microencapsulated mixture of thickening agents, disintegrating agents and pharmaceutically active substances.

NSAIDs inhibit prostaglandin (PG) synthesis by blocking the action of cyclooxygenase (COX), which exists in two forms. COX-1 is present in virtually all tissues and synthesizes PG which provides GI mucosal protection. COX-2 is activated in response to cytokines and other inflammatory factors. NSAIDs currently available inhibit both COX-1 and COX-2 to varying degrees. Selective COX-2 inhibitors, Vioxx (rofecoxib) and Celebrex (celecoxib) were promoted to provide pain relief and avoid GI complications. However, all NSAIDs, including COX-2 inhibitors, can cause GI adverse events, including life-threatening perforations, ulcers or bleeds. One study comparing Vioxx to naproxen detected a four fold risk of myocardial infarction. Nissen S E, et al, *JAMA* 2001; 286:954-959. Vioxx has now been withdrawn from the market. COX-2 isoenzymes are necessary for maintaining renal blood flow. COX-2 inhibitors have been reported too cause acute renal failure.

Platelets play an important role in the development of atherosclerosis. COX-2 inhibitors reduce the levels of prostacyclin (PGI2), a cyclooxygenase product that inhibits platelet activation and may accelerate atherosclerosis. Nonselective NSAIDs suppress both thromboxane and prostacyclin and retard atherogenesis. Pratico D, *Proc Natl Acad Sci USA* 2001; 98:3358-3363. The cardioprotective effects of ASA are not seen with COX-2 inhibitors, which do not inhibit TXA2 production by platelets. Hart C, *Modern Drug Discovery* May/June 1999.

ASA in addition to its well-appreciated ability to inhibit PG and TX, can also switch on the production of the body's own anti-inflammatory lipid mediators, namely aspirin-triggered lipoxins. ASA acetylates COX-2 and re-directs COX-2's catalytic activity away from generating intermediates of prostaglandins and thromboxanes and towards producing another compound (15R-HETE), which is converted to 15-epi-Lipoxin A4 by 5-lipoxygenase in activated neutrophils and then rapidly released. The new compound is termed aspirin-triggered 15-epi-lipoxin A4 (ATL) is unique to aspirin, as other widely used NSAIDs are unable to generate ATL. Both Lipoxin A4 and ATL act at the low nanomolecular concentration range via interaction with a specific cell surface receptor (denoted the Lipoxin A4 receptor) and possess potent protection in peritonitis, dermal inflammation, reprofusion injury, periodontitis and angiogenesis. ATL formation within the vasculature is relevant in the cardioprotective actions of aspirin. ATL may protect against the initial inflammatory events that could lead to deleterious cardiovascular effects. Chiang N, Serhan C N, *Discovery Medicine* 2004; 4(24):470-475.

In 2-23% of adults with asthma, and rarely in children with aspirin, aspirin and NSAIDs cause asthma exacerbations. Prompt administration of intramuscular epinephrine is the usual treatment for systemic anaphylaxis and asthma. Epinephrine administered orally is inactivated in the GI tract. Epinephrine delivered by a fast dissolving tablet would be absorbed by the buccal mucosa and pass directly into the systemic circulation avoiding the first-pass effect. In rabbit studies a 2.5 mg sublingual epinephrine tablet reached a peak of effectiveness at 20.8 minutes, while an injection of epinephrine reached peak effectiveness in 15.8 minutes. Gu X, Simons K J, Simons F E. *Biopharmaceutics & Drug Disposition* 2002; 23:213-216. A fast dissolving tablet with 0.15-20 mg of epinephrine is an alternative method of prevention and treating endothelial dysfunction associated with the inflammation associated with asthma and anaphylactic shock.

Aspirin is contraindicated in patients with influenza because of the association of aspirin and influenza and Reye syndrome. One solution is to combine antiviral drugs with the NSAID, amino sugar and zinc compound. Influenza virus targets the endothelial cells and is linked to hemagglutin, myocarditis and myositis. Feldmann A, et al *J Virol* 2000 September; 74(17):8018-27. The neuraminidase inhibitors, such as amantadine, rimantadine, zanamivir and oseltamivir, are a new class of antiviral agents that interfere with the replication of influenza A and B. Neuraminadase (NA) is a critical protein of the surface membrane of the influenza virus. The flu virus consists primarily of RNA molecules wrapped in proteins. Once a virus has invaded a cell and multiplied new virus particles emerge from the cell bound together. One viral protein, and enzyme called neuraminidase, is required for the bundle to unglue itself so that individual virus particles can infect other cells. Zanamivir foils the flu by binding to neuraminidase and deactivating it, so that the virus particles stay bundled. Even in young adults, a flu shot is at best 70-90% effective. Among elderly people, whose immune response is weakened, the vaccine is only 30-50% effective. Neuraminidase inhibitors may work against the virus even as flu shots fail because it will still be able to dock to neuraminidase's conserved site. The addition of a neuraminidase inhibitor to the composition may offer the prevention of endothelial dysfunction from the influenza virus.

ASA has also been reported to be effective in reducing the risk of gastric cancer. Zaridze D, *Int J Cancer* 1999; 82:473-476. ASA has also been reported to be effective against diabetic retinopathy, Alzheimers Disease, colon and rectal cancer, deep vein thrombosis, kidney failure, migraine headaches, cataracts, gallstones, and insect bites. Life-long use of low-dose aspirin prevents inflammatory and endogenous oxidative insults accompanying aging and attempt to increase maximum and mean life span.

Aspirin is an inexpensive, anti-inflammatory, antioxidant compound that effects the immune system and cardiovascular health. Aspirin affects oxidant production, cytokine responses and blocks glycosidation reactions, thus posing as a triple threat against the symptoms of aging. Phillips T, Leeuwenburgh C. Lifelong aspirin supplementation as a means to extending life span. *Rejuvenation Research* 2004; 7(4):343-252. Long-term use of low dose aspirin may double the chances of individuals living a healthy life into their 90s. Aspirin use may reduce the risk of breast cancer by 20%, lung cancer by 30%, colorectal cancer and prostate cancer by 50%. Aspirin may reduce the risk of Alzheimer's disease, cataract, gallstones, reflux esophagitis, oral gum deterioration and prolong both the quantity and quality of life. Morgan G. A quantitative illustration of the public health potential of aspirin. *Medical Hypothesis* 2003; 60(6):900-902.

It is one object of this invention to incorporate an NSAID, such as ASA, to provide pain relief and anti-inflammatory and anti-thrombotic benefits to prevent and treat endothelial dysfunction.

One of the gastrointestinal (GI) side-effects of nonsteroidal anti-inflammatory drugs (NSAIDs), is aggravating or initiating colitis type disorders, and explained by the hypothesis that NSAIDs inhibit glucosamine synthetase resulting in a reduction of the glucoaminoglycan (GAG) layer of the GI tract. The GAG layer is mechanical, located in the pre-endothelial and sub-endothelial area in the arterial network, and an electrostatic barrier, due to the negative charges from the highly anionic GAGs. The neutralization of the electrostatic barrier, results in a breakdown of the GAG defense, resulting in an increase in extravasation of body fluids into the intestinal lumen and also the passage of toxins and large foreign molecular weight antigens into the circulation. Russell A L, *Medical Hypothesis* 1999; 52(4):297-301. There is a close histological and pathophysiological association with endothelial membrane changes in GI disorders and the endothelium of the vasculature. An atheroma occurs due to a defect in GAG function at the inflammation site of the endothelium allowing the defect to be saturated with cholesterol. Aminosugars such as glucosamine, chondroitin and synthetic mucopolysaccharide pentosam sulfate have been shown to replace the GAG layer and improve GI and vascular inflammatory disorders. Rheumatoid arthritis is believed due to increased permeability of the GI tract. Glucosamine, for purposes of this invention, may be regarded as a preventative of endothelium dysfunction.

Amino sugars, for purposes of this invention, consist of but are not limited to; glucosamine, glucosamine sulphate, glucosamine hydrochloride, N-acetylglucosamine and Poly-Nag. Glucosamine, which is formed in the body as glucosamine-6-phosphate (G6-P), is a building block for glycolipids, glycoproteins, glycosaminoglycans, hyaluronate and proteoglycans. It is an essential component of cell membranes and cell surface proteins as well as interstitial structural molecules that hold cells together.

Glucosamine is a small molecule, very soluble in water, and 90% absorbed in the GI tract. Glucosamine sulfate (GS) appears to be linked to its ability to stimulate the synthesis of proteoglycans needed to stabilize cell membranes and increase intracellular ground substance. Since the anti-inflammatory ability of GS is different than that of NSAIDs, it is possible the two might have a synergistic effect in alleviating some types of inflammation. Evidence indicates a combined treatment utilizing glucosamine with an NSAID can decrease the amount of NSAID required to produce an anti-exudative result by a factor of 2-2.7 times with preservation of activity. Kelly G S, *Alt Med Rev* 1998; 3(1):27-39.

The dosage range for glucosamine can vary from 200 mg to 3000 mg per day, in divided doses, for the treatment and prevention of endothelial dysfunction, osteoarthritis and inflammation, depending on body weight and severity of symptoms. The usual dosage is 20-50 mg per fast dissolving tablet based on the amount of ASA used in each dosage. In a rapidly disintegrating tablet the amount of glucosamine to protect the lining of the mouth and gastric mucosa is reduced due to the rapid absorption of the ASA in the oral cavity. Glucosamine administered in a fast disintegrating tablet may prevent endothelial dysfunction. Dosage of 100-200 mg per tablet based on the amount of fast disintegrating material used is disclosed.

The use of amino sugars, such as glucosamine, is well known in the art. Jacobi, U.S. Pat. No. 3,859,436, discloses a topical composition of glucose, fructose, glucosamine and desoxyribose and ribose. Prudden, U.S. Pat. No. 4,006,224, discloses a method for treating ulcerative colitis with d-glucosamine. Henderson, U.S. Pat. No. 5,364,845, discloses a composition for the repair of connective tissue with glucosamine, chrondroitin sulfate and manganese. Sherman et al, U.S. Pat. No. 6,117,851, discloses a method for treating osteoarthritis.

It is a further object of this invention to incorporate an amino sugar, such as glucosamine, to enhance the GAG defense, anti-inflammatory properties, and synergistic effect with NSAIDs to treat and prevent endothelial dysfunction.

Zinc is known to have gastroprotective effects in both humans and experimental animals. Gastric lesions were induced in rats by the intragastric administration of indomethacin. Mucosal ulcerations were completely prevented by pre-treatment with zinc sulphate. These protective effects result from the inhibition of lipid peroxidation and the preservation of mucosal nitric oxide synthase. Joseph R M, Varela V, Kanji V K, Subramony C, Mihas A A, *Aliment Pharmacol Ther* 1999 February; 13(2):203-8. Zinc sulphate taken orally was shown to heal gastric ulcers at three times the rate of a placebo. Zinc sulphate taken orally appears to act by the local action of zinc ions on the gastric mucosa. Frommer D J, *Med J of Australia* 1975; 2:793-796.

Zinc compounds have anti-inflammatory and anti-infective properties. Zinc has an inhibitory effect on the release of histamine from mast cells due to its stabilizing effect of the mast cell membrane. Mast cells isolated from specimens of atherosclerotic plaques contained matrix metalloproteinase type 9, one of the enzymes that can produce collagen degradation. Kovanen P t, et al. *J. Am College of Cardiology* 1998; 32:606-612. Zinc can inhibit the growth of Streptococci and *Actinomyces* bacteria when used as a dentifrice. Zinc compounds have antiseptic, antifungal, antiviral and astringent properties. As an astringent, zinc can be used therapeutically to arrest hemorrhage by coagulating blood, check diarrhea, reduce inflammation of mucus membranes, promote healing, toughen skin and decrease sweating. Zinc's dominant biological action is membrane stabilization. The inhibitory effect of zinc on allergy and immunology make it an excellent enhancement to glucosamine and chondroitin therapy.

One of the side effects of ASA is salicylate inducted hearing loss and tinnitus. The inner ear has the highest concentration of zinc in the body. Studies have suggested that a zinc deficiency can cause a hearing-nerve impairment and tinnitus. Shambaugh G E Jr., *Am J Otol* 1989 March; 10(2):156-60. Salicylate-induced hearing loss was completely prevented by the simultaneous administration of zinc. Gunther T, Rebentisch E, Vormann J, *J Trace Elem Electrolytes Health Dis* 1989 March; 3(1):51-3. Zinc was also found to be useful in treating tinnitus. Ochi K, Ohashi T, et al *Nippon Jibiinkoka Gakkai Kaiho* 1997 September:100(9):915-9.

In a preferred form of the invention, the composition uses a zinc salt with the dosage range of 5 to 60 mg per day in divided doses, and may be combined with an NSAID such as aspirin or by itself in a fast disintegrating tablet. Zinc salts are selected from a group consisting of, but not limited to: zinc sulfate, zinc chloride, zinc acetate, zinc phenol sulfonate, zinc borate, zinc bromide, zinc nitrate, zinc glycerophosphate, zinc benzoate, zinc carbonate, zinc carnosine, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate.

It is a further object of this invention to incorporate a zinc compound, such as zinc gluconate or sulphate, to reduce inflammation, prevent gastric ulceration, prevent toxic side effects of NSAIDs, and treat and prevent endothelial dysfunction. The amount of a zinc compound is reduced when a rapidly disintegrating tablet is used because the agents are absorbed in the oral cavity.

Hypertension contributes to endothelial dysfunction, particularly in coronary vessels. Mild hypertension is defined as a systolic pressure of 140 to 159 mm Hg and a diastolic pressure of 90 to 99 mm Hg. Untreated hypertension increases the incidence of stroke, coronary events, heart and renal failure and shortens life expectancy. Atherosclerosis is much more likely to appear in those parts of the circulatory system subjected to the highest blood pressure. In human hypertension, endothelial dysfunction has been documented in peripheral and coronary macro- and microcirculation and in renal circulation. Taddei S et al, *J Cardiovasc Pharmacol* 1998; 32 Suppl (3):S41-7.

Dietary supplements are products that people add to their diets and comprise; vitamins, minerals, herbs and other botanicals, amino acids, fatty acids, substances such as enzymes, organ tissues, glandulars and metabolites and other substances meant to improve ones diet. Dietary supplements that have been associated with improving exercise tolerance and recovery, lowering blood pressure and improving endothelial dysfunction and immune dysfunction. Supplements include, but are not limited to; calcium, magnesium, potassium, Coenzyme Q10, Vitamin A, B vitamins, Vitamin C, Vitamin D, Vitamin E, Vitamin K2, L-arginine, citrulline, flaxseed and fish oils, taurine, garlic, chromium, L-glutamine, glutathione, selenium, alpha-lipoic acid, folic acid, hawthorn, licorice extract, pantothenic acid, zinc salts, branched-chain amino acids (leucine, isoleucine, valine, etc), melatonin, resveratrol, C12 peptide, aliphatic alcohols such as policosanol and octacosanol and various herbs, roots, phospholipids and botanicals.

Reversing oxidative stress and the subsequent inhibition of lipid peroxidation should improve endothelial dysfunction. Vitamin E supplements, 600 mg per day, in a double-blind trial showed improvement in endothelial-dependent dilation of the brachial artery. Vitamin C improved vascular dysfunction in diabetics. The combined effects of Vitamin C and E prevented endothelial dysfunction during transient hyperglycemia after oral glucose loading in healthy subjects. Guerci B, et al, *Diabetes Metab (Paris)* 2001, 27: 436-447.

Vasoprotective supplements such as Vitamins C and E, calcium, omega-3 fatty acids, L-arginine, citrulline, folic acid will improve endothelial function. Supplementation with folic acid and vitamin B12 improved brachial artery endothelium-dependent dilation in patients with CHD and that this action may be mediated through reduced concentrations of free plasma homocysteine. Chambers J C, et al, *Circulation* 2000; 102:2479-2483. B vitamins (folic acid, vitamin B6, vitamin B12) reduce homocysteine that cause endothelial dysfunction, impair vascular reactivity, promote inflammatory processes leading to age-related macular degeneration (AMD) and atherosclerosis. The combination of folic acid (2.5 mg), vitamin B6 (50 mg) and vitamin B12 (1 mg) reduced the risk of confirmed AMD by 34% and the risk of visually significant AMD by 41% over 7.3 years. Vitamin B12 is best delivered by ODT to be absorbed by the buccal mucosa due to denaturation of vitamin B12 by gastric juices.

Ascorbic acid (Vitamin C) reverses endothelial motor dysfunction in patients with coronary artery disease. Investigators found that long-term ascorbic acid treatment has a sustained beneficial effect on endothelium-derived nitric oxide action. Vita J A, *Circulation* 1999; 99:3234-3240. Vitamin C was also found to reverse endothelial function in cardiomyopathy. Figulla H R, et al, *Am J Cardio* 2001; 88:1001-1005. Doses of 500 mg/day lowered systolic blood pressure by 10% after one month.

Coenzyme Q10 (CoQ), a natural substance produced by the body, belongs to a family of compounds called quinones. CoQ therapy in doses of 50 mg/twice a day can reduce blood pressure and stabilize blood glucose levels. Hodgson J M, *Eur J Clin Nutr* 2002; 56:1137-1142. Similar results were obtained with calcium salts and alpha-lipoic acid supplementation. Vasdev S, et al, *J Hypertens* 2000 May; 18(5):567-73.

Magnesium intake of 10 to 40 mmol is associated with reductions in blood pressure. Miller ER, et al, *Am J Hypertens* 2002; 15:691-696. Oral magnesium and potassium salts contribute to the electrical stability of the heart. Zehender M, et al, *J Am Coll Cardiol* 1997; 29:1028-1034. Magnesium oral doses range from 10-50 mg but can be reduced with fast dissolving tablets. Potassium supplementation can prevent and treat hypertension, especially in those who are unable to reduce their sodium intake. Whelton P K, *Semin Nephrol* 1999 September; 19(5):494-9. Modest increases in dietary potassium of 48 to 60 mmol/day lowers blood pressure in elderly hypertensive subjects. Fotherby M D, *Int J Clin Pract* 1997 June; 51(4):219-22.

The enzyme nitric oxide synthase generates nitric oxide (NO) from the amino acid L-arginine. NO is responsible for vasodilator tone in the coronary arteries and the regulation of blood pressure in the systemic arteries. Arginine supplementation reverses endothelial dysfunction and lowers blood pressure. Siani A, et al, *Am J Hypertens* 2000 May; 13(5 Pt 1):547-51. Oral dose of L-arginine ranges for 50-5,000 mg.

Citrulline, an amino acid, like arginine can be converted into nitric oxide. Citrulline is transformed in the kidneys to arginine and necessary for endothelial health. Oral doses for citrulline ranges from 50-600 mg.

Taurine reverses endothelial dysfunction, and restored endothelial function in smokers to that of nonsmokers. Taurine has a protective effect on endothelial structure and function and restores nitric oxide synthase protein expression. Fermessy F M et al. *Circulation* 2003; 107:410-415.

Melatonin inhibits NO production both in vivo and in vitro. It inhibits bradykinin-induced NO production by endothelial cells. Low levels of melatonin are associated with an increased risk of adverse cardiovascular events after myocardial infarction. Melatonin regulates cycles of sleep and wakefulness and has been reported to reduce tinnitus. Dosage can range from 0.5-5.0 mg.

Casein-derived protein hydrolysate (C12 Peptide) has angiotensin-converting enzyme (ACE) inhibiting properties and can also reduce plasma angiotensin II and aldosterone levels. Dosage can range from 25-1,500 mg.

Policosanol is a mixture of higher primary aliphatic alcohols isolated from sugar cane, whose main component is octacosanol, is known to reduce systolic and diastolic blood pressure. This supplement also inhibits platelet aggregation and has cholesterol lowering properties. Mas R, et al, *Asia Pac J Clin Nutr* 2004; 13(Suppl):S101. Gluni-Berthold I, Berthold H K, *Am Heart J* 2002 February; 143(2):356-65.

To the mixture may also be added; dyes, flavorings, cranberry extract, grapeseed extract, blueberry extract, sweeteners, pigments, antioxidants, antibacterial agents, anti-inflammatory agents, effervescent salts, probiotics, prebiotics, bismuth compounds, such as those known to persons skilled in the art may be added in amounts sufficient to impart their particular characteristic.

The above-mentioned patents are hereby incorporated by reference.

Orally disintegrating tablet (ODT) technology consists of a solid dosage form containing medicinal substances which rapidly dissolves, usually in less than 60 seconds when placed on the tongue. Since 40% of the population have difficulty swallowing pills, many do not take their medications. The ODT can be made by many techniques, including direct compression, wet granulation and lyophilization. Sugar based excipients such as mannitol, sorbitol, dextrose, fructose and zylitol are blended with disintegrants such as microcrystalline cellulose, effervescent agents, alginic acid and crospovidone.

Absorption of therapeutic agents from the oral cavity provides direct entry into the systemic circulation, thus avoiding the first-pass effect of the liver and degradation in the gastrointestinal tract. It is estimated that the permeability of the buccal mucosa of the oral cavity is 4 to 4000 times greater than that of the skin. ODT provides many advantages over the use of regular pills that must be digested in the GI tract.

The compositions may be in the form of chewable tablets. They may be formulated from compressible carbohydrates comprising mannitol, sorbitol, dextrose, sucrose and mixtures thereof, combined with binders such as cellulose, starch, gums, gelatin, fats and oils. Sweeteners, flavors and color agents may be added to the active agent or drug and compressed into a chewable tablet.

The compositions may be in the form of a powder that is added to water or other liquid for swallowing. Effervescent salts may be added to the composition along with flavor an color agents.

Many variations of the present invention will suggest themselves to those skilled in the art in light of the above-detailed description. All such obvious modifications are within the full intended scope of the appended claims. This invention is further illustrated by the following examples which are to be regarded as illustrative only, and in no way limit the scope of the invention.

Example 1
Fast dissolving tablet for aspirin

| | |
|---|---|
| Acetylsalicylic acid | 81 mg |
| Mannitol | 120 mg |
| Sorbitol | 100 mg |
| Crospovidone | 30 mg |
| Glucosamine sulfate | 25 mg |
| Aspartame | 5 mg |
| Zinc gluconate | 5 mg |
| Stearic acid | 2 mg |
| Magnesium stearate | 2 mg |

The fast dissolving tablet in Example 1 provides aspirin for rapid absorption by the buccal mucosa.

Example 2
Fast dissolving tablet for aspirin, extra strength

| | |
|---|---|
| Acetylsalicylic acid | 160 mg |
| Mannitol | 120 mg |
| Sorbitol | 100 mg |
| Crospovidone | 30 mg |
| Glucosamine sulfate | 25 mg |
| Aspartame | 5 mg |
| Zinc gluconate | 5 mg |
| Stearic acid | 2 mg |
| Magnesium stearate | 2 mg |

The fast dissolving tablet in Example 2 provides an extra strength aspirin for rapid absorption by the buccal mucosa.

EXAMPLE 3

Fast dissolving tablet for aspirin.

| | |
|---|---|
| Acetylsalicylic acid | 81 mg |
| Mannitol | 120 mg |
| Sorbitol | 100 mg |
| Crospovidone | 30 mg |
| Aspartame | 5 mg |
| Zinc gluconate | 5 mg |
| Stearic acid | 2 mg |
| Magnesium stearate | 2 mg |

The fast dissolving tablet in Example 3 provides aspirin for rapid absorption by the buccal mucosa with a zinc salt.

EXAMPLE 4

Fast dissolving tablet for aspirin

| | |
|---|---|
| Acetylsalicylic acid | 81 mg |
| Mannitol | 120 mg |
| Sorbitol | 100 mg |
| Crospovidone | 30 mg |
| Glucosamine sulfate | 25 mg |
| Aspartame | 5 mg |
| Stearic acid | 2 mg |
| Magnesium stearate | 2 mg |

The fast dissolving tablet in Example 4 provides aspirin for rapid absorption by the buccal mucosa with an amino sugar.

EXAMPLE 5

Fast dissolving tablet for aspirin with an agent that suppresses gastric acid formation.

| | |
|---|---|
| Acetylsalicylic acid | 81 mg |
| Mannitol | 120 mg |
| Dextrose | 100 mg |
| Crospovidone | 30 mg |
| Glucosamine sulfate | 25 mg |
| Misoprostol | 20 mg |
| Aspartame | 5 mg |
| Zinc gluconate | 5 mg |
| Stearic acid | 2 mg |
| Magnesium stearate | 2 mg |

The fast dissolving tablet in Example 5 provides aspirin and an agent that suppresses gastric acid formation for rapid absorption by the buccal mucosa.

EXAMPLE 6

Fast dissolving tablet with ibuprofen for those with influenza

| | |
|---|---|
| Ibuprofen | 100 mg |
| Mannitol | 120 mg |
| Sucrose | 100 mg |
| Crospovidone | 30 mg |
| Glucosamine sulfate | 25 mg |
| Amantadine | 25 mg |
| Aspartame | 5 mg |
| Zinc gluconate | 5 mg |
| Stearic acid | 2 mg |
| Magnesium stearate | 2 mg |

The fast dissolving tablet in Example 6 provides an NSAID for those who may have influenza combined with an antiviral to prevent endothelial dysfunction.

EXAMPLE 7

Fast dissolving tablet with aspirin for lowering blood pressure and/or providing cardiovascular protection

| | |
|---|---|
| Mannitol | 120 mg |
| Sucrose | 100 mg |
| Magnesium taurate | 100 mg |
| Acetylsalicylic acid | 81 mg |
| Potassium citrate | 50 mg |
| Crospovidone | 30 mg |
| Glucosamine sulfate | 25 mg |
| Vitamin E | 25 mg |
| Aspartame | 5 mg |
| Coenzyme Q10 | 5 mg |
| Vitamin B3 | 5 mg |
| Vitamin B6 | 5 mg |
| Zinc gluconate | 5 mg |
| Stearic acid | 2 mg |
| Policosanol | 2 mg |
| Magnesium stearate | 2 mg |
| Folic acid | 80 mcg |
| Vitamin B12 | 20 mcg |

The fast dissolving tablet in Example 7 provides a composition of blood pressure lowering and/or cardiovascular protection with lipid lowering dietary supplements and aspirin.

EXAMPLE 8

| Fast dissolving tablet for lowering blood pressure | |
|---|---|
| Mannitol | 120 mg |
| Sucrose | 100 mg |
| Magnesium taurate | 100 mg |
| Potassium citrate | 50 mg |
| Crospovidone | 30 mg |
| Glucosamine sulfate | 25 mg |
| Vitamin E | 25 mg |
| Aspartame | 5 mg |
| Coenzyme Q10 | 5 mg |
| Vitamin B3 | 5 mg |
| Vitamin B6 | 5 mg |
| Zinc gluconate | 5 mg |
| Stearic acid | 2 mg |
| Resveratrol | 2 mg |
| Magnesium stearate | 2 mg |
| Policosanol | 2 mg |
| Vitamin K2 | 20 mcg |
| Folic acid | 80 mcg |
| Vitamin B12 | 20 mcg |

The fast dissolving tablet in Example 8 provides a composition of blood pressure lowering and/or cardiovascular protection with lipid lowering dietary supplements.

EXAMPLE 9

| Fast dissolving tablet for improving exercise recovery | |
|---|---|
| Mannitol | 120 mg |
| Sucrose | 100 mg |
| Magnesium taurate | 100 mg |
| Potassium citrate | 50 mg |
| Crospovidone | 30 mg |
| Glucosamine sulfate | 25 mg |
| Vitamin E | 25 mg |
| Creatine | 25 mg |
| Sodium chloride | 10 mg |
| Bromelain | 5 mg |
| Aspartame | 5 mg |
| Coenzyme Q10 | 5 mg |
| Vitamin B3 | 5 mg |
| Vitamin B6 | 5 mg |
| Zinc gluconate | 5 mg |
| Stearic acid | 2 mg |
| Magnesium stearate | 2 mg |
| Folic acid | 80 mcg |
| Vitamin B12 | 20 mcg |

The fast dissolving tablet in Example 9 provides a composition of supplements to prevent endothelial dysfunction and improve exercise tolerance and recovery.

EXAMPLE 10

| Fast dissolving tablet for improving exercise recovery | |
|---|---|
| Mannitol | 120 mg |
| Sucrose | 100 mg |
| Potassium citrate | 50 mg |
| Citrulline | 50 mg |
| Crospovidone | 30 mg |
| Leucine | 25 mg |
| Creatine | 25 mg |
| Isoleucine | 15 mg |
| Valine | 15 mg |
| Sodium chloride | 10 mg |
| Bromelain | 5 mg |
| Aspartame | 5 mg |
| Zinc gluconate | 5 mg |
| Stearic acid | 2 mg |
| Magnesium stearate | 2 mg |

EXAMPLE 10-continued

| Fast dissolving tablet for improving exercise recovery | |
|---|---|
| Folic acid | 80 mcg |
| Vitamin B12 | 20 mcg |

The fast dissolving tablet in Example 10 provides a composition of supplements to prevent endothelial dysfunction and improve exercise tolerance and recovery.

EXAMPLE 11

| Fast dissolving tablet for asthma or anaphylactic shock | |
|---|---|
| Mannitol | 120 mg |
| Sucrose | 100 mg |
| Crospovidone | 30 mg |
| Aspartame | 5 mg |
| Epinephrine | 5 mg |
| Stearic acid | 2 mg |
| Magnesium stearate | 2 mg |

The fast dissolving tablet in Example 11 provides a composition to treat asthma and anaphylactic shock.

EXAMPLE 12

| Fast dissolving tablet for a zinc compound | |
|---|---|
| Mannitol | 120 mg |
| Sucrose | 100 mg |
| Crospovidone | 30 mg |
| Vitamin E | 25 mg |
| Aspartame | 5 mg |
| Zinc acetate | 5 mg |
| Zinc gluconate | 4 mg |
| Stearic acid | 2 mg |
| Magnesium stearate | 2 mg |

The fast dissolving tablet in Example 12 provides a composition to treat endothelial dysfunction.

EXAMPLE 13

| Fast dissolving tablet for an amino sugar | |
|---|---|
| Glucosamine | 200 mg |
| Mannitol | 120 mg |
| Sucrose | 100 mg |
| Crospovidone | 30 mg |
| Vitamin E | 25 mg |
| Aspartame | 5 mg |
| Stearic acid | 2 mg |
| Magnesium stearate | 2 mg |

The fast dissolving tablet in Example 13 provides a composition to treat endothelial dysfunction.

EXAMPLE 14

| Fast dissolving tablet containing melatonin and prevent endothelial dysfunction. | |
|---|---|
| Mannitol | 120 mg |
| Sucrose | 100 mg |
| Crospovidone | 30 mg |
| Aspartame | 5 mg |
| Melatonin | 1 mg |

EXAMPLE 14-continued

| Fast dissolving tablet containing melatonin and prevent endothelial dysfunction. | |
|---|---|
| Stearic acid | 2 mg |
| Magnesium stearate | 2 mg |

The fast dissolving tablet in Example 14 provides a composition to treat *H. pylori* infection and endothelial dysfunction.

EXAMPLE 15

| Powder composition for aspirin | |
|---|---|
| Acetylsalicylic acid | 81 mg |
| Mannitol | 50 mg |
| Sorbitol | 50 mg |
| Crospovidone | 30 mg |
| Glucosamine sulfate | 25 mg |
| Calcium carbonate | 10 mg |
| Aspartame | 5 mg |
| Zinc gluconate | 5 mg |
| Stearic acid | 2 mg |
| Magnesium stearate | 2 mg |

The powder composition in Example 15 is added to a liquid and absorbed by the buccal mucosa and gastrointestinal tract.

EXAMPLE 16

| Chewable tablet for aspirin | |
|---|---|
| Acetylsalicylic acid | 81 mg |
| Mannitol | 120 mg |
| Sorbitol | 100 mg |
| Microcrystalline cellulose | 80 mg |

EXAMPLE 16-continued

| Chewable tablet for aspirin | |
|---|---|
| Glucosamine sulfate | 25 mg |
| Hydrolyzed gelatin | 10 mg |
| Aspartame | 5 mg |
| Zinc gluconate | 5 mg |
| Stearic acid | 2 mg |
| Magnesium stearate | 2 mg |

The chewable tablet in Example 16 provides aspirin for those with difficulty swallowing regular tablets and has absorption by the buccal mucosa.

EXAMPLE 17

| Fast dissolving tablet containing probiotics to treat H. pylori infections and prevent endothelial dysfunction. | |
|---|---|
| Mannitol | 120 mg |
| Sorbitol | 100 mg |
| Lactobacillus acidophilus (5 billion units) | 100 mg |
| Crospovidone | 30 mg |
| Aspartame | 5 mg |
| Stearic acid | 2 mg |
| Magnesium stearate | 2 mg |

The fast dissolving tablet of Example 17 provides a composition to treat *H. pylori* infection and endothelial dysfunction.

What is claimed is:

1. A method of treating endothelial dysfunction associated with asthma or anaphylactic shock by administering a rapidly disintegrating tablet to mammals comprising; epinephrine, mannitol, crospovidone, flavor, and sweetener.

\* \* \* \* \*